(12) United States Patent
Denyer et al.

(10) Patent No.: US 8,608,090 B2
(45) Date of Patent: Dec. 17, 2013

(54) NEBULIZER METERING CHAMBER

(75) Inventors: Jonathan S. H. Denyer, Chichester (GB); Anthony Dyche, Hayling Island (GB)

(73) Assignee: Profile Drug Delivery Limited, West Sussex (GB)

( * ) Notice: Subject to any disclaimer, the term of this patent is extended or adjusted under 35 U.S.C. 154(b) by 1124 days.

(21) Appl. No.: 10/185,365

(22) Filed: Jun. 26, 2002

(65) Prior Publication Data

US 2003/0146300 A1    Aug. 7, 2003

(30) Foreign Application Priority Data

Jan. 18, 2002 (GB) .................................. 0201150.0

(51) Int. Cl.
*B05B 1/08* (2006.01)
(52) U.S. Cl.
USPC .......................... 239/102.1; 239/86; 239/350
(58) Field of Classification Search
USPC ............................. 239/86, 102.1, 102.2, 350
See application file for complete search history.

(56) References Cited

U.S. PATENT DOCUMENTS

| | | | | |
|---|---|---|---|---|
| 845,175 A | * | 2/1907 | Hutchins | 222/425 |
| 2,064,726 A | * | 12/1936 | Brown | 239/350 |
| 2,349,894 A | * | 5/1944 | Wells | 239/350 |
| 2,835,533 A | * | 5/1958 | Baker | 239/346 |
| 2,892,576 A | * | 6/1959 | Ward | 222/402.2 |
| 3,155,141 A | * | 11/1964 | Doyle et al. | 431/67 |
| 3,591,090 A | * | 7/1971 | Carden | 239/305 |
| 3,642,213 A | * | 2/1972 | Parkison et al. | 239/590 |
| 3,668,905 A | * | 6/1972 | Schlunke | 68/5 D |
| 4,083,496 A | | 4/1978 | Oshima et al. | |
| 4,086,057 A | * | 4/1978 | Everett | 422/128 |
| 4,961,885 A | * | 10/1990 | Avrahami et al. | 261/142 |
| 5,312,281 A | * | 5/1994 | Takahashi et al. | 446/25 |
| 6,062,212 A | * | 5/2000 | Davison et al. | 128/200.16 |
| 6,116,517 A | * | 9/2000 | Heinzl et al. | 239/101 |
| 6,119,953 A | | 9/2000 | Gañán-Calvo et al. | |
| 6,164,565 A | * | 12/2000 | Adee et al. | 239/333 |
| 6,237,589 B1 | | 5/2001 | Denyer et al. | |
| 6,367,450 B1 | | 4/2002 | Kato | |

FOREIGN PATENT DOCUMENTS

| | | |
|---|---|---|
| EP | 0627266 A2 | 12/1994 |
| EP | 97927296 A1 | 4/1999 |
| EP | 99950992 | 8/2001 |
| EP | 1142600 A1 | 10/2001 |
| FR | 1 395 676 A | 4/1965 |
| GB | 428423 | 5/1935 |
| GB | 428432 | 5/1935 |
| GB | 1164602 | 9/1969 |
| WO | WO92/09322 | 6/1992 |
| WO | WO-95 20411 A | 8/1995 |
| WO | WO95/31237 | 11/1995 |
| WO | WO-98 29321 A | 7/1998 |
| WO | WO99/38770 | 8/1999 |
| WO | WO 99/63946 | 12/1999 |
| WO | WO 00/38770 | 7/2000 |
| WO | WO00/63946 | 10/2000 |

* cited by examiner

*Primary Examiner* — Christopher Kim
(74) *Attorney, Agent, or Firm* — Timothy A. Nathan

(57) ABSTRACT

A nebulizer includes nebulization device for nebulizing a substance and a reservoir having a metering chamber arranged so as to feed a substance to be nebulized to the nebulization device and a second chamber arranged to hold and retain any of this substance in excess of the volume held in the metering chamber.

25 Claims, 4 Drawing Sheets

FLUID SENSOR

NEBULIZER METERING CHAMBER

BACKGROUND OF THE INVENTION

1. Field of the Invention

The present invention relates to nebulizers, for example, for atomizing a drug for inhalation by patient, whereby the atomized drug is administered to a patient through deposition in his lungs, and to methods of loading nebulizers. The subject and may be a powder, a liquid, or a particulate suspension, but is not limited only to these three forms of substance. In this specification, references to the drug being in a particular form, such as "liquid" or "droplet" is to be understood to also include the other forms, unless specified otherwise.

2. Brief Description of Art

Several different types of nebulizer are known, the most common being pneumatically operated nebulizers which are operated from a compressed air source connected to the nebulizer. Other types of nebulizer include ultrasonic type nebulizers which use a piezo electric crystal to atomize the substance, mesh-type nebulizers which force the substance in liquid form through a fine mesh in order to create droplets, electrohydrodynamic (EHD) nebulizers and capillary microjet nebulizers.

For medical use where a drug is delivered to the lungs of a patient, the optimum diameter of the medication particles or droplets is about 1-5 microns. If the particles or droplets are bigger than this, they tend to impact the patient's airways before they reach the lungs, but if they are smaller than this range, they enter the lung during inhalation, and tend to be carried out of the lungs again on exhalation without sedimenting in the lungs. For the best result, as greater proportion of the drug must reach and sediment as deep inside the lung as possible.

Each of the types of nebulizer has its own advantages and disadvantages. For example, common pneumatic type nebulizers are typically only 50% efficient at releasing the nebulized drug in suitable sized droplets from the reservoir, and require baffles to collect oversized droplets which coalesce and run back into the reservoir for recirculation. By contrast, mesh-type nebulizers will often have an efficiency of around 90%. Other types of nebulizer also have a high efficiency, where a very high proportion of the nebulizer drug is in the correct droplet size range, such as electrohydynamic nebulizers and capillary microjet nebulizers. None of these nebulizers needs to re-circulate the drug, and so they might be described as single pass nebulizers.

However, pneumatic nebulizers can be developed to have an output rate which does not vary significantly throughout the life of the apparatus, which means that the amount of drug delivered to a patient during a treatment can be measured accurately so that when the prescribed amount of drug has been delivered to the patient's lungs, nebulization can automatically stop. One such measurement arrangement is known as Adaptive Aerosol Delivery™, and is present in a nebulizer sold by Medic-Aid Limited under the name Halolite, and is the subject of European Patent Application No. 97927296 and European Patent Application No. 99950992, the contents of both of which we incorporate herein by reference in their entireties.

However, the output rate of a mesh-type nebulizer will often deteriorate over the life of the nebulizer since the mesh holes may become blocked, which affects the rate of delivery. Therefore, a pre-calibrated rate of nebulizer output as used in the Adaptive Aerosol Delivery™ system described briefly above is not always appropriate. Instead, it is appropriate to fill a reservoir with a pre-set dose for delivery to the patient. Once all of the dose has been delivered, the treatment is complete. The same issue applies to EHD nebulizers and capillary microjet nebulizers in terms of the number of sites of aerosol generation varying over the lifetime of the product. In the EHD system, any disruption n the electrostatic field generated can cause the production of fewer cones which form the nebulization sites, and this will change the output rate. In the case of capillary microjet nebulizers, a large number of microjets are required, usually several hundred, to produce an aerosol with sufficient mass output. Blockage of individual microjets will affect the rate of output of the produce.

Since pneumatic nebulizers are much more popular than mesh-type nebulizers, many existing drug preparations have been developed for pneumatic nebulizers, but the volume of drug in these preparations is far too great for use with mesh-type nebulizers. Clearly, it is important for safe use of these devices that a simple and reliable method of metering the drug is used.

WO 99/63946 discloses a mesh-type nebulizer, the operation of which is bet seen in FIG. 3 of that application. A mesh is mounted across an aperture, and the nebulizer is arranged such that piezo electric element is used to vibrate the mesh. When a droplet of liquid is placed on the rear surface of the mesh, the vibrations from the piezo electric element causes the liquid to pass through the holes in the mesh forming droplets which are released from the front surface of the mesh.

EP 1142600 A1 discloses a spray forming device in which a liquid is fed through a pipe into a narrow space between a mesh and a piezo electric element. The mesh includes holes through which the liquid passes when the piezo electric element vibrates.

Examples of EHD and capillary microjet nebulizers can be found in WO 00/38770 and U.S. Pat. No. 6,119,953 respectively, which are incorporated herein by reference in their entireties.

A pneumatic nebulizer is shown in EP 0627266 A2 in which air from a pressurized air source issues from an air outlet hole around which are disposed holes through which the liquid to be atomized is drawn out from a main reservoir. Each of those holes is within a groove forming a secondary reservoir around the air outlet hole. A deflector bar is located across and in the path of the air issuing from the air outlet so that as it issues from the air outlet, it is immediately deflected across the top of the liquid outlet holes, thereby creating low pressure regions, thereby drawing the liquid up from the main reservoir beneath, and atomizing that liquid as it is drawn from the holes. The droplets generated in this way are carried to a patient fro inhalation. Atomization can be switched on and off by switching on and off the pressurized air supply to the nebulizer.

BRIEF SUMMARY OF THE INVENTION

According to a first aspect of the invention, a nebulizer includes a nebulization device for nebulization a substance; and a reservoir having 1) a metering chamber arranged to feed the substance to be nebulized to the nebulization device for nebulization, and 2) a second chamber arranged to hold and retain any of the substance in excess of the volume held in the metering chamber. This allows a unit dose of vial of a substance to be nebulized to be poured into the reservoir, but only the metered volume of the metering chamber to be nebulized during the treatment since the remainder or excess of the substance is retained in the second chamber. This allows single pass type nebulizers to be used in conjunction with a very much greater number of drug preparations than is currently possible. It can, of course, also be used where exactly the correct volume of drug is supplied, since this will merely fill the metering chamber, without overflowing into the second chamber.

It is preferred that a barrier be disposed between the metering chamber and the second chamber. This has the advantage of being relatively simple in construction, and allows the excess drug to be retained in the second chamber only once the barrier has been put in place.

It is also preferred that the barrier is a sealing element for location between the metering and second chambers. In the preferred embodiment, the barrier also includes an air vent through which air is permitted to enter the metering chamber to replace the substance as it is nebulized.

It is advantageous to include a lid arranged to close the reservoir and it is further preferred that the barrier is carried by the lid so that when the lid is shut, the barrier automatically separates the metering chamber and second chamber.

Advantageously, the metering chamber may include a rim against which the barrier can form a seal. There may also be advantages in having the base of the second chamber below the top of the metering chamber.

According to another embodiment, the reservoir includes an overflow port at the top of the metering chamber which leads to the second chamber. In this case, the overflow port could be arranged around all, or a substantial proportion, of the top of the metering chamber. A lid may be included to close the reservoir, and an air vent may be included which permits air to enter reservoir.

It is also preferred that a sensor is included which is arranged to sense when the substance to be nebulized has all, or substantially all, been nebulized, and if a controller is included, the controller will stop the operation of the nebulization device once the sensor has sensed that all or substantially all of the substance has been nebulized.

The nebulizer is preferably a single pass type nebulizer. For example, it may be a nebulizer wherein the nebulization device includes a mesh through which the substance is nebulized, or may include a plurality of capillaries through which the substance is nebulized. Alternatively, the nebulization device may include an electrostatic field generator by which the substance is nebulized. All of these types of nebulizer nebulize the substance without re-circulation of the substance, particularly large droplets, back to the reservoir for re-nebulization.

According to a second aspect of the invention a method of loading a nebulizer having a nebulization device comprises the steps of pouring a substance to be nebulized into a reservoir of the nebulizer and retaining any of the substance in the reservoir in excess of what is required so that it will not be fed to the nebulization device.

It is preferred that the method further comprise the step of placing a barrier in the reservoir to retain the excess substance, and that barrier might be placed to retain the excess substance upon closing a lid of the reservoir.

BRIEF DESCRIPTION OF THE DRAWINGS

Embodiments of the present invention will now be disclosed by way of example only with reference to the drawings in which.

It should be understood that this invention relates to any type of single pass type of nebulizer. In the following embodiments, mesh-type nebulizers are described by way of example, but the invention applies also to other single pass nebulizers.

DETAILED DESCRIPTION OF THE INVENTION

Figure 1:
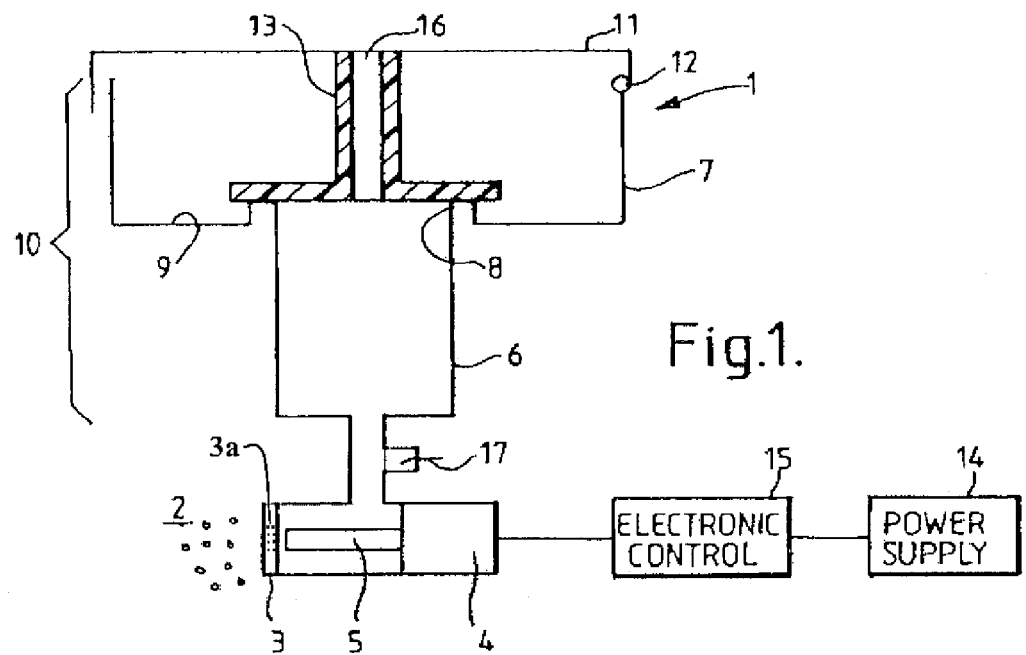
FIG. 1 is a schematic view of a mesh-type nebulizer according to the present invention.

A nebulizer according to a first embodiment is shown in FIG. 1, and part of this nebulizer is shown during operation in FIGS. 2 to 5. In FIG. 1, the nebulizer 1 is a mesh-type nebulizer which generates an aerosol 2 of a drug preparation through a mesh plate 3 by using an ultrasonic transducer 4 to drive a horn 5 to vibrate in the region of the mesh plate 3. The horn 5 is located close to the rear face of the mesh plate 3, and is caused to vibrate by the ultrasonic transducer 4, whereby the aerosol 2 is generated from the front face of the mesh plate 3. A substance to be atomized into an aerosol 2 is in fluid contact with the rear face of the mesh plate 3, and it is this that is driven through the holes 3a of the mesh plate 3 by the vibrating horn 5.

During each treatment, a certain volume of the substance to be atomized is located in a metering chamber 6 which is located above the mesh plate 3 in order to feed the substance to be atomized to its rear face. A fluid sensor 17 is located between the metering chamber 6 and the mesh plate 3 such that, once the substance to be atomized has almost all been aerosolized, this is detected so that the ultrasonic transducer 4 may be switched off at the end of treatment once the substance to the atomized has all or substantially all been atomized.

Above the metering chamber 6 is an upper chamber 7. The metering chamber has a top rim 8 located within the upper chamber 7, and the base 9 of the upper chamber 7 is located outwardly from the rim 8 of the metering chamber. Together, the upper chamber 7 and the metering chamber 6 constitute a fluid reservoir 10.

At the top of the upper chamber 7, a lid 11 is attached via a hinge 12, and which closes the top of the upper chamber 7. The hinge 12 will be closed positively by way of some form of catch (not shown). Depending from the lid 11 is a sealing element/barrier 13 which engages with the rim 8 of the metering chamber, and at least part of the seal is made from an elastomeric material whereby the seal may be formed between the sealing element 13 and the rim 8. The sealing element 13 is intended to prevent liquid from moving between the upper chamber 7 and the metering chamber 6 while the lid 11 is closed. It is for this reason that it is advantageous to have the lid 11 closing positively such as by a catch so that the seal is maintained while the lid 11 is shut.

The lid 11 and sealing element 13 include an air vent 16 which, as the atomizer operates, allows the level of liquid within the metering chamber 6 to drop.

A power supply 14 is used to power the atomizer since power is required to drive the aerosolization. An electronic controller 15 controls the ultrasonic transducer 4 so that, for example, once the fluid sensor 17 senses that there is no liquid remaining to be atomized, the ultrasonic transducer 4 will be switched off. In addition, a more sophisticated control device can be used here such that the patient's breathing is measured, and atomization only occurs during the inhalation part of a patient breathing pattern. Details of such control systems are described in European Patent Publication No. 0910421, and are used in the Halolite nebulizer made by Medic-Air Limited, and more details can be found in European Patent Application No. 99950992. In these applications, the duration of each breath is measured, and an average inhalation period for the last three breaths is calculated. On the subsequent breath, the aerosolized drug is released for a proportion of the calculated average inhalation period, typically 50%. That way, all of the drug that is released will actually reach the lungs of the patient, rather than remaining in the upper airways and being exhaled before reaching the lungs where it should be deposited.

It will be appreciated from the introductory part of this patent specification that since some types of nebulizers, such as mesh-type, EHD type and microjet capillary type nebulizers, are more efficient than most pneumatic nebulizers at releasing a drug, available drug preparations provide too much drug for use in those nebulizers, and since the output rate from those nebulizers changes through the life of the nebulizer, Adapted Aerosol Delivery™ is not appropriate to monitor the amount of drug the patient is receiving.

The operation of the nebulizer of FIG. 1 will now be described with reference to FIGS. 2 to 5, from which it will be understood how the present invention overcomes the difficulties associated with the prior art nebulizers that are available.

Figure 2:
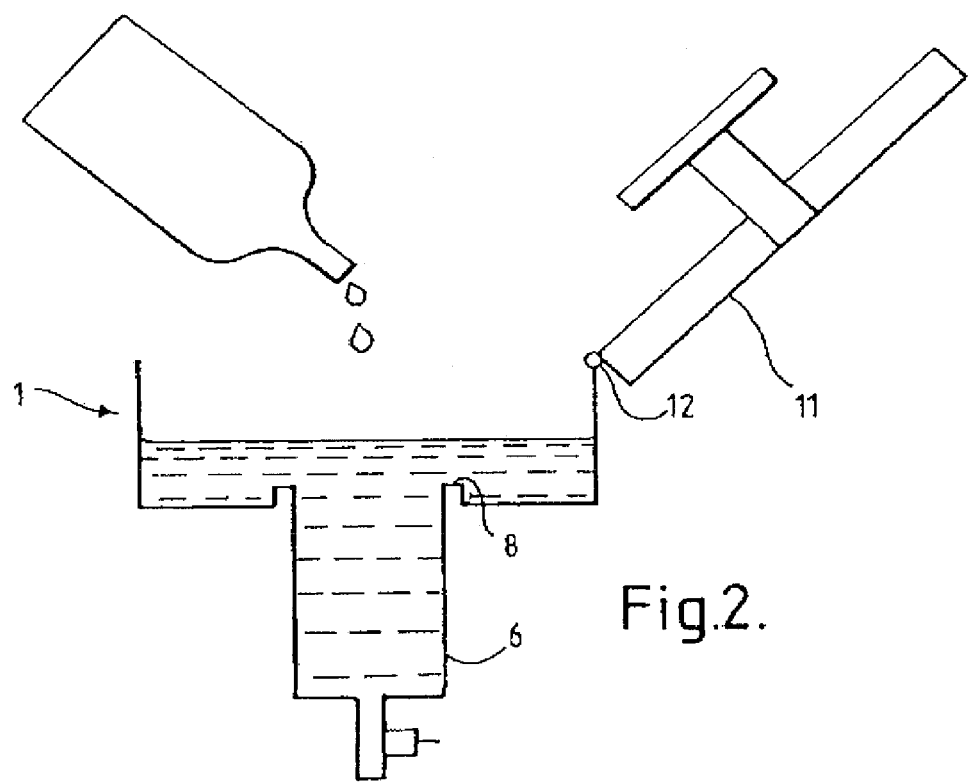
FIG. 2 is a schematic view of part of the nebulizer of FIG. 1, during filling.
Figure 3:
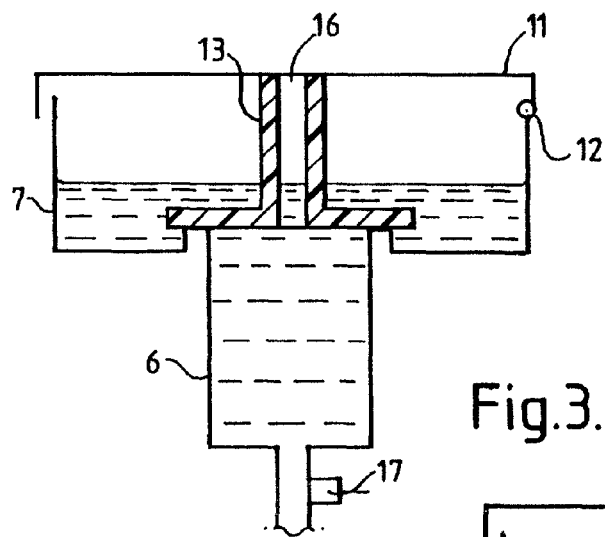
FIG. 3 is a schematic view of part of the nebulizer of FIG. 1, after filling.

With most drugs for delivery by atomization into the lungs of a patient, the drug preparation is a liquid of a certain volume which is packaged in a drug vial. The volume of drug which is to be delivered to a patient's lungs is equal to the volume of the metering chamber 6, but the volume in the vial will normally be much greater. With reference to FIG. 2, the lid is opened which removes the sealing element 13 from within the fluid reservoir 10. The liquid drug can then be poured into the field reservoir 10 where it will fill all of the metering chamber 6, and part of the upper chamber 7. It is necessary to close the lid 11 of the upper chamber 7 at this point in order to restrict the amount of the drug which can reach the mesh plate 3. To do this, the lid 11 is simply shut so that the sealing element 13 forms a seal against the rim 8 of the metering chamber 6. Thus, the liquid in the upper chamber 7 is completely separated from the liquid in the metering chamber 6, as shown in FIG. 3.

Figure 4:
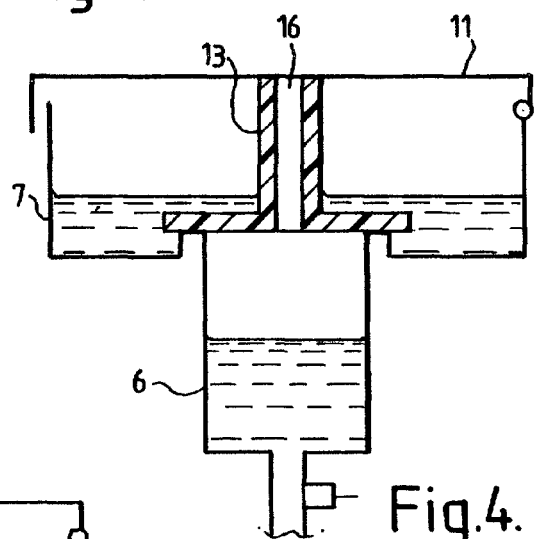
FIG. 4 is a schematic view of part of the nebulizer of FIG. 1, during use.

In FIG. 4 it will be seen that about half of the liquid has been atomized, and the level of the liquid within the metering chamber 6 has dropped. The air vent 16 in the lid 11 allows air to enter the metering chamber 6 to replace the liquid being atomized, but without drawing in liquid from the upper chamber 7.

Figure 5:
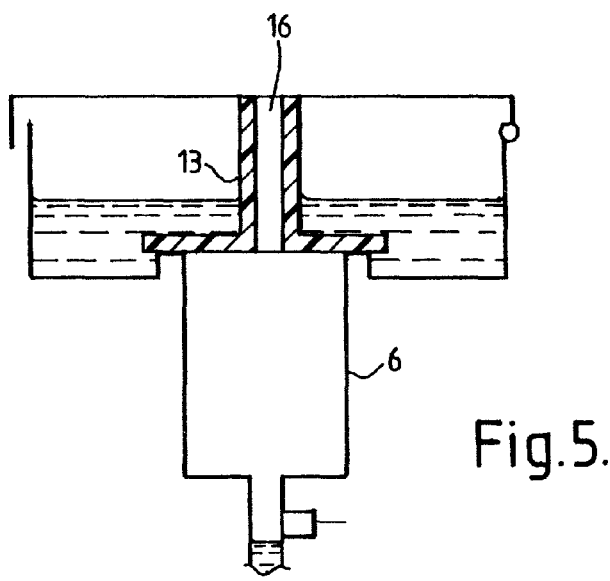
FIG. 5 is schematic view of part of the nebulizer of FIG. 1 on completion of delivery of the drug.

In FIG. 5, it will be seen that the liquid within the metering chamber 6 has dropped so low that the sensor 17 is no longer covered by the liquid and so atomisation will be stopped. At this point, the electronic controller 15 knows that treatment is complete, and even if the patient repeatedly opens and closes the lid 11 after this time, the electronic controller 15 will not allow treatment to recommence.

A suitable sensor 17 is disclosed in International Patent Application No. WO 99/17888, which is a simple electrical circuit using two electrodes in contact with the fluid and which detects the electrical current passing through the circuit when the fluid is in contact with the electrodes. Various well known liquid sensors could be used here in place of this one.

Figure 6:
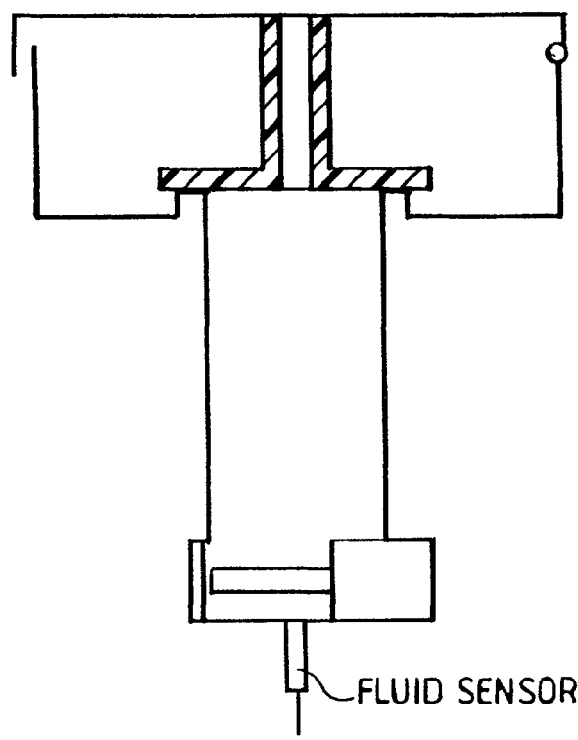
FIG. 6 shows a second embodiment of a mesh-type nebulizer according to the present invention.

With reference now to FIG. 6, this Figure shows an arrangement very similar to that shown in FIG. 1, except that the fluid sensor is shown at the very bottom, much closer to the mesh plate 3. Also, in this case the neck between the metering chamber 6 and the back face of the mesh plate 3 has been removed such that the metering chamber 6 leads directly to the mesh plate 3. Just as in FIG. 1, the mesh plate 3 is gravity fed from the metering chamber 6. Placing the liquid sensor at the very bottom of the chamber is possible if the arrangement of the fluid flow around the ultrasonic mesh plate 3 is optimized to minimize residual volume. This will minimize the residual volume of liquid in the system at the end of treatment, and may make it easier to clean the device.

Of course, the use of liquid sensors is not the only way of measuring when all of the liquid has been atomized. For example, as an alternative, it is possible to determine from the ultrasonic control electronics when all of the liquid at the mesh has been atomized by monitoring the frequency and amplitude of vibration. This will be very different when there is no liquid to when a substance is being atomized and this could be used in place of the sensor 17.

Figure 7:
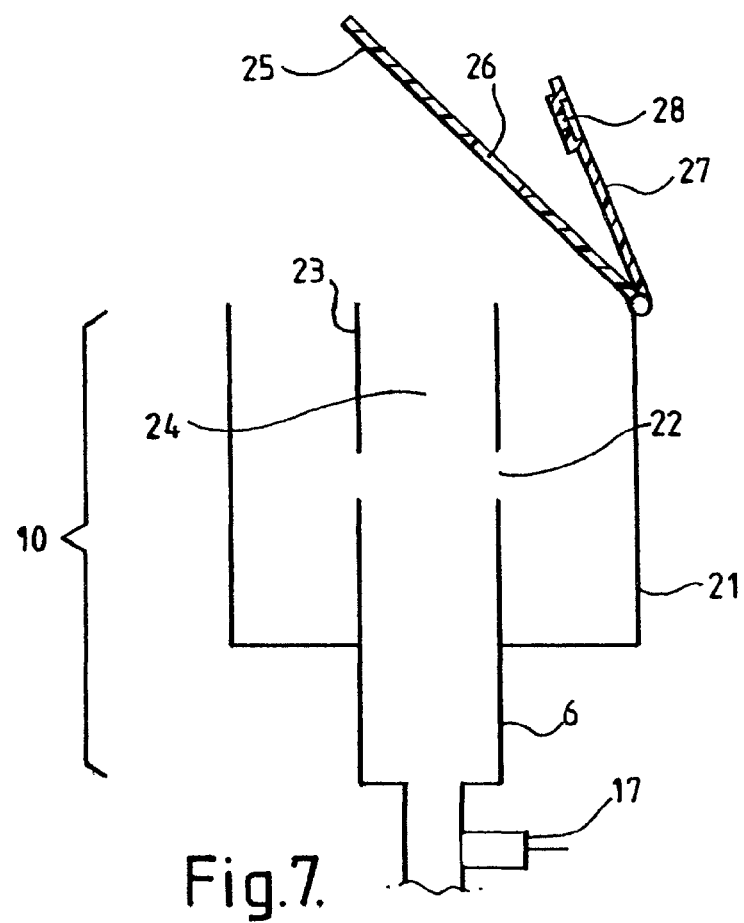
FIG. 7 is a schematic view of a third embodiment with an overflow port.
Figure 8:
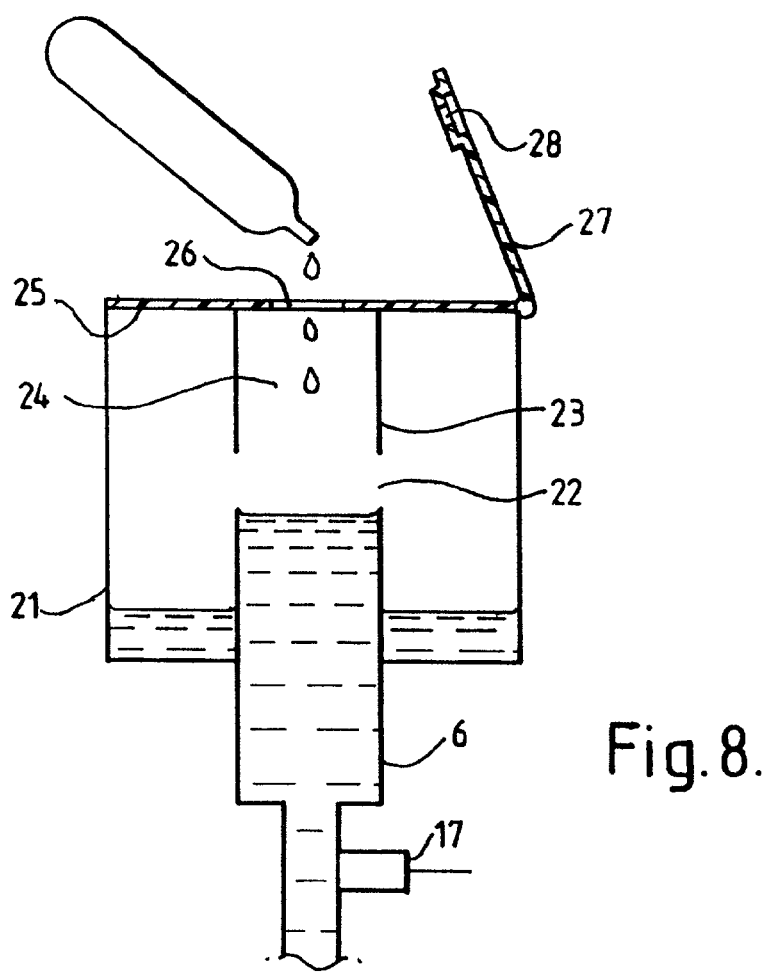
FIG. 8 is a schematic view of the nebulizer of FIG. 7 during filling.
Figure 9:
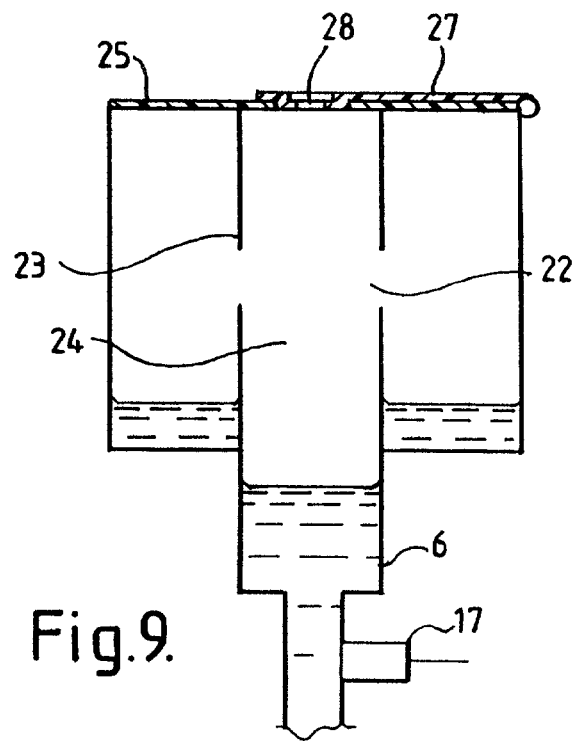
FIG. 9 is a schematic view of the nebulizer of FIG. 7 during nebulization.

FIGS. 7, 8 and 9 show a further embodiment of the invention. Referring first to FIG. 7, the nebulization device including the mesh plate horn and ultrasonic transducer are not shown, but they can be arranged in the same way as shown in FIG. 1. In FIG. 7, the same reference numerals are used as in FIG. 1, where possible.

In FIG. 7, the fluid chamber 10 includes the metering chamber 6 as in the earlier embodiment, but the arrangement of the other chamber is different. In this case, the other chamber 21 is an overflow chamber disposed around the metering chamber 6. At the top of the metering chamber 6 is an overflow port 22, which in this case is shown as a port which extends right of way around the top of the metering chamber 6. However, the port 22 may not be as extensive as this, and could be just a single relatively small port arranged to allow any excess of the substance to be atomized to overflow into the overflow chamber 21. The upper edge of the overflow port 22 is defined by a tube 23 which defines a passage 24 which generally aligns with the metering chamber 6. The purpose of passing 24 will become clearer below when FIG. 8 is described.

The top of the fluid reservoir 10 is closed by a lid 25 which fits over the top of the overflow chamber. The lid 25 includes an interior edge defining a central hole 26 which coincides with the passage 24. The lid 25 is mounted to pivot about hinge. It is also desirable to be able to close the central hole 26, and this is achieved by virtue of a filling lid 27 which is also pivotally mounted about the hinge. This filling lid 27 can be opened to allow the nebulizer to be filled, and subsequently closed to prevent entry of foreign material, and also to prevent spillage. The filling lid 27 includes an air vent 28.

With reference to FIG. 8, the nebulizer is shown during a filling operation. Firstly, the filling lid 27 is lifted in order to open the passage 24. A unit dose vial is then opened and the contents are poured into the nebulizer through the passage 24. The liquid from the vial is directed into the metering chamber by the tube 23, so as to fill the metering chamber 6, and any liquid in excess of that overflows via the overflow port 22 into the overflow chamber 21. Once the unit dose vial is empty, the filling lid 27 can be closed, and the atomizer can then be used. The liquid level within the metering chamber 6 will fall as the liquid is atomized, with air being allowed to enter the fluid reservoir 10 via the air vent 28 in the filling lid 27.

FIG. 9 shows the fluid reservoir 10 as the level of liquid within the metering chamber drops. The liquid within the overflow chamber 21 is retained in the overflow chamber. Once treatment is complete, the lid 25 is opened, and the excess substance can be emptied, and the device washed.

In the embodiments described above, the ultrasonic transducer causes the horn to vibrate. Of course, it is possible to alter this arrangement somewhat. For example, instead of vibrating the horn, atomization could be achieved by vibrating the mesh plate instead. Both of these arrangements fall within the term mesh-type nebulizers.

While the invention has been described above with reference to specific embodiments thereof, it is apparent that many changes, modifications, and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A nebulizer including:
a nebulization device configured to aerosolize a substance; and
a reservoir having 1) a metering chamber arranged so as to feed a substance to be nebulized to the nebulization device, wherein the metering chamber is sized to retain a metered volume of the substance as the substance is poured into the nebulizer, and 2) a second chamber substantially surrounding the metering chamber, the second chamber being constructed and positioned relative to the metering chamber so as to hold and retain any of the substance that overflows the metering chamber in excess of the volume held in the metering chamber when the substance is poured into the nebulizer, wherein the nebulizer is shaped and configured such that the volume of substance contained in the second chamber is not fed to the nebulization device while the nebulizer nebulizes substance fed from the metering chamber.

2. A nebulizer comprising:
a reservoir having a metering chamber and a second chamber,
a nebulization device constructed and arranged to nebulize substance from the metering chamber; and
a barrier movable relative to the reservoir between first and second positions, the barrier being constructed and positioned to be manually movable from the first position into the second position after a substance has been poured into the reservoir and while the substance is disposed in the reservoir,
wherein, when the barrier is in the first position and the substance is poured into the reservoir, a volume of the substance that exceeds a metered volume of the metering chamber will flow into the second chamber, and
wherein, when the barrier is in the second position, the barrier isolates the metering chamber from the second chamber such that the barrier prevents fluid flow from the second chamber to the metering chamber.

3. The nebulizer of claim 2, wherein the barrier comprises an air vent that is constructed and arranged such that when the barrier is in its second position, the air vent allows ambient air from outside of the nebulizer to enter the metering chamber through the air vent.

4. The nebulizer of claim 2, wherein the nebulization device is constructed and arranged to nebulize substance into a particle size small enough for delivery to a patient's lungs when the patient inhales the nebulized substance.

5. The nebulizer of claim 2, wherein the nebulization device is constructed and arranged to nebulize substance into particles, the particles comprising particles having a diameter of between 1 and 5 microns.

6. The nebulizer of claim 2, wherein:
the barrier comprises a sealing element,
when the barrier is in the second position, e sealing element forms a seal between the metering chamber and the second chamber, and
when the barrier is in the first position, the sealing element does not form a seal between the metering chamber and the second chamber.

7. The nebulizer of claim 2, further comprising an air vent extending between the metering chamber and ambient air outside of the nebulizer, the air vent being constructed and arranged to allow ambient air from outside of the nebulizer to enter the metering chamber through the air vent while the nebulization device is nebulizing substance from the metering chamber.

8. The nebulizer of claim 2, further comprising a reservoir lid movable between open and closed positions relative to the reservoir,
wherein barrier is carried by the lid such that movement of the lid between the open and closed positions moves the barrier between the barrier's first and second positions, respectively.

9. The nebulizer of claim 2, wherein the metering chamber includes a rim against which the barrier forms a seal when the barrier moves into its second position.

10. The nebulizer of claim 2, further including a sensor which is arranged to sense when the substance in the metering chamber has all, or substantially all, been nebulized.

11. The nebulizer of claim 2, wherein the nebulizer is a single-pass nebulizer.

12. The nebulizer of claim 2, wherein:
the nebulization device comprises a vibrator and a plate having a plurality of holes therein, and
the nebulization device is constructed and arranged to nebulize substance by using the vibrator to drive the substance through the plurality of holes of the plate, whereby movement of the substance through the plurality of holes causes nebulization of the substance.

13. The nebulizer of claim 12, wherein the vibrator comprises an ultrasonic transducer.

14. The nebulizer of claim 12, wherein:
the vibrator is configured to vibrate the plate, and
the nebulization device is configured such that vibration of the plate nebulizes the substance from the metering chamber.

15. The nebulizer of claim 12, wherein the metering chamber and plate are configured and positioned relative to each other such that substance in the metering chamber is gravity fed to the plate.

16. The nebulizer of claim 2, wherein the metering chamber and nebulization device are configured and positioned relative to each other such that substance in the metering chamber is gravity fed to the nebulization device.

17. The nebulizer of claim 2, wherein the second chamber substantially surrounds a rim of the metering chamber such that the volume of the substance that exceeds the capacity of the metering chamber will flow into the second chamber.

18. A nebulizer comprising:
a reservoir having a metering chamber and a second chamber, the metering chamber and second chamber being shaped and configured such that when a substance is poured into the reservoir, a volume of the substance that exceeds a capacity of the metering chamber will flow into the second chamber;

a single-pass nebulization device constructed and arranged to nebulize substance from the metering chamber; and a barrier constructed and arranged to prevent fluid flow from the second chamber to the metering chamber while the nebulizer nebulizes a substance from the metering chamber.

19. The nebulizer of claim 18, wherein:

the nebulization device comprises a vibrator and a plate having a plurality of holes therein, and the nebulization device is constructed and arranged to nebulize substance from the metering chamber by using the vibrator to drive the substance through the plurality of holes, whereby movement of the substance through the plurality of holes causes nebulization of the substance.

20. The nebulizer of claim 19, wherein the vibrator comprises an ultrasonic transducer.

21. The nebulizer of claim 19, wherein:

the vibrator is configured to vibrate the plate, and the nebulization device is configured such that vibration of the plate nebulizes the substance from the metering chamber.

22. The nebulizer of claim 19, wherein the metering chamber and plate are configured and positioned relative to each other such that substance in the metering chamber is gravity fed to the plate.

23. The nebulizer of claim 18, wherein the metering chamber and nebulization device are configured and positioned relative to each other such that substance in the metering chamber is gravity fed to the nebulization device.

24. The nebulizer of claim 18, wherein the nebulizer is constructed and arranged to prevent substance nebulized by the nebulization device from flowing into the reservoir.

25. The nebulizer of claim 18, wherein the metering chamber and second chamber are shaped and configured such that when a substance is poured into the metering chamber, a volume of the substance that exceeds a capacity of the metering chamber will flow from the metering chamber into the second chamber.

* * * * *